US007384961B2

(12) United States Patent
Bloms-Funke et al.

(10) Patent No.: US 7,384,961 B2
(45) Date of Patent: Jun. 10, 2008

(54) SATURATED AND UNSATURATED HETEROARYLCYCLOALKYLMETHYL AMINES AS ANTI-DEPRESSANTS

(75) Inventors: Petra Bloms-Funke, Wuerselen (DE); Claudia Puetz, Dueren (DE); Ivars Graudums, Stolberg (DE); Achim Kless, Aachen (DE); Carsten Griebel, Aachen (DE); Hagen-Heinrich Hennies, Simmerath (DE); Dagmar Kaulartz, Stolberg (DE); Sabine Reinardy, Wuerselen (DE); Derek Saunders, Aachen (DE); Klaus Schiene, Duesseldorf (DE); Bernd Sundermann, Aachen (DE); Werner Englberger, Stolberg (DE); Oswald Zimmer, Wuerselen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/155,766

(22) Filed: Jun. 20, 2005

(65) Prior Publication Data
US 2006/0025456 A1 Feb. 2, 2006

Related U.S. Application Data

(63) Continuation of application No. PCT/EP2003/014653, filed on Dec. 19, 2003.

(30) Foreign Application Priority Data
Dec. 20, 2002 (DE) ............................... 102 61 091

(51) Int. Cl.
*A61K 31/44* (2006.01)
*A61K 31/13* (2006.01)
*C07D 401/00* (2006.01)

(52) U.S. Cl. ...................... 514/336; 514/663; 546/268.1
(58) Field of Classification Search .............. 546/268.1; 514/336, 663
See application file for complete search history.

(56) References Cited

U.S. PATENT DOCUMENTS

| 4,021,560 | A | 5/1977 | Yardley |
| 4,833,143 | A | 5/1989 | Armitage et al. |
| 5,811,582 | A | 9/1998 | Buschmann et al. |

FOREIGN PATENT DOCUMENTS

| DE | 19609847 | 9/1997 |
| EP | 1010689 | 6/2000 |
| GB | 765874 | 1/1957 |

OTHER PUBLICATIONS

Barrett et. al., "Aminoalkyl Tertiary Carbinols and Derived Products. Part VIII. Some 1-Alkyl- and 1:2-cyclo Alkano-pyrrocolines." Journal of the Chemical Society (1958) 338-49.*

Radl et. al., "Synthesis and antinociceptive activity of some 3-chlorophenyl- and 6-chloro-2-pyridinyl derivatives", Collection of Czechoslovak Chemical Communications, (1999), 64 (2), 377-388.*
Stanislav Rádl et al., "Synthesis and Antinociceptive Activity of Some 3-Chlorophenyl- and 6-Chloropyridin-2-YL Derivatives", Collection of Czechoslovak Chemical Communications, 1999, pp. 377-388, vol. 64, Academic Press, London, Great Britain, XP009006162.
M.J. O'Neil, "Citalopran", The Merck Index, 13th Edition, 2001, Merck Research Laboratories, Whitehouse Station, New Jersey, USA, ISBN: 0911910-13-1, XP-002275249.
Pal Pacher et al., "Current Trends in the Development of New Antidepressants", Current Medicinal Chemistry, 2001, pp. 89-100, vol. 8, No. 2, 2001 Bentham Science Publishers Ltd.
R.D. Porsolt et al., "Behavioural Despair in Mice: A Primary Screening Test for Antidepressants", Arch. Int. Pharmacodyn., 1977, pp. 327-336, vol. 229.
Eric W. Fish et al., "Distress Vocalizations in Maternally Separated Mouse Pups: Modulations Via $5\text{-}HT_{1A}$, $5\text{-}HT_{1B}$, and $GABA_A$ Receptors", Psychopharmacology, 2000, pp. 277-285, vol. 149, Springer-Verlag 2000.
International Search Report dated Apr. 8, 2004.
Andrew W. Goddard et al., "Principles of the Pharmacotherapy of Anxiety Disorders", Anxiety Disorders, pp. 548-563, Neurobiology of Mental Illness, Chapter 39, 1999.
S.H. Sindrup, "Antidepressants as Analgesics", Anesthesia: Biologic Foundations, 1997, pp. 987-997, Chapter 64, Lippincott-Raven Publishers, Philadelphia, PA, USA.
A.F. Casy et al., "Tertiary Alcohols and Related Compounds Derived from 2-Dimethylaminomethylcyclohexanone", pp. 3635-3638, 1964, Chapter 702.

(Continued)

*Primary Examiner*—Janet L. Andres
*Assistant Examiner*—Binta Robinson
(74) *Attorney, Agent, or Firm*—Crowell & Moring LLP

(57) ABSTRACT

Saturated and unsaturated heteroarylcycloalkylmethyl-amine compounds corresponding to formula I,

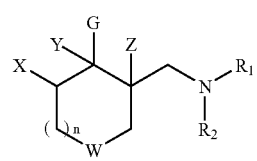

processes for their preparation, pharmaceutical formulations comprising these compounds and the use of saturated and unsaturated heteroarylcycloalkylmethyl-amines for the preparation of pharmaceutical formulations. pharmaceutical formulations and related methods of treatment or prophylaxis of certain condition, especially depression and/or pain, are also disclosed.

21 Claims, No Drawings

OTHER PUBLICATIONS

P.A. Barrett et al., Aminoalkyl Tertiary Carbinols and Derived Products, pp. 338-349, Part VIII, Amino alkyl Tertiary, Chapter 63 1958.

E. G. Gray et al., "The Isolation of Nerve Endings from Brain: an Electron-Microscopic Study of Cell Fragments Derived by Homogenization and Centrifugation", Journal of Anatomy, 1962, pp. 79-88, vol. 96, Part 1.

Martin Ch. Frink et al., "Influence of Tramadol on Neurotransmitter Systems of the Rat Brain", Arzneimittel-Forschung/Drug Research, 1996, pp. 1029-1036, vol. 46 (II), No. 11, Germany.

Yung-Chi Cheng et al., "Relationship Between the Inhibition Constant ($K_1$) and the Concentration of Inhibitor which Causes 50 Per Cent Inhibition (/50) of an Enzymatic Reaction", Biochemical Pharmacology, 1973, pp. 3099-3107, vol. 22, Pergamon Press, Great Britain.

Hans Lineweaver et al., "The Determination of Enzyme Dissociation Constants", Mar. 1934, pp. 658-666, vol. 56.

David Dubuisson et al., "The Formalin Test: A Quantitative Study of the Analgesic Effects of Morphine, Meperidine, and Brain Stem Stimulation in Rats and Cats", Pain, 1977, pp. 161-174, vol. 4, Elsevier/ North-Holland Biomedical Press.

* cited by examiner

SATURATED AND UNSATURATED HETEROARYLCYCLOALKYLMETHYL AMINES AS ANTI-DEPRESSANTS

CROSS REFERENCE TO RELATED APPLICATIONS

This application is a continuation of International Patent Application No. PCT/EP2003/014653, filed Dec. 19, 2003, designating the United States of America, and published in German as WO 2004/063161 A1, the entire disclosure of which is incorporated herein by reference. Priority is claimed based on German Patent Application No. 102 61 091.6, filed Dec. 20, 2002.

FIELD OF THE INVENTION

The present invention relates to saturated and unsaturated heteroarylcycloalkylmethyl-amines, processes for their preparation, pharmaceutical formulations comprising these compounds and the use of saturated and unsaturated heteroarylcycloalkylmethyl-amines for the preparation of pharmaceutical formulations as well as related methods of treatment, especially for depression and/or pain.

BACKGROUND OF THE INVENTION

Depression is an affectivity disorder with which a depressive syndrome occupies the foreground, depressive meaning associated with depression or of a sad mood. Depressive diseases include unipolar mild depressions, dysthymia, melancholy, bipolar depressions, severe depressions with or without madness and moderate depressions (bipolar disease I, mania and severe depression; bipolar disease II, hypomania and severe depressions; cyclothymic personality disorders, hypomania and mild depressions). Those antidepressants of which the antidepressant action is based on an inhibition of the re-uptake of the monoamines noradrenaline (NA) or serotonin (5-HT) are widely used for therapy of depressions (Pacher, P., Kohegyi, E., Kecskemeti, V., Furst, S., Current Medicinal Chemistry 2001, 8, 89-100). Inhibitors of the re-uptake of monoamines are also used for treatment of anxiety disorders (Goddard, A. W., Coplan, J. D., Gorman, J. M., Charney, D. S., in: Neurobiology of mental illness, Charney, D. S., Nestler, E. J., Bunney, B. S. (eds.), Oxford University Press, New York, 1999, p. 548-563). Anxiety disorders are classified into generalized anxiety disorders, panic attacks, obsessive syndromes, social anxiety disorders, simple phobias, agoraphobias and posttraumatic stress disorders (PTSD).

In addition to the actual antidepressant action, inhibitors of the re-uptake of noradrenaline and serotonin also lead to an independent analgesic action by activating descendant pain inhibition paths at the level of the spinal cord. Inhibitors of the re-uptake of monoamines are employed clinically for monotherapy, and also as an adjuvant for treatment of chronic pain (inter alia neuropathic pain) (Sindrup, in: Yaksh, T. L. et al., Anesthesia. Biological foundations. Philadelphia: Lippincott-Raven, 1997, 987-997). There is still an urgent need for treatment of chronic pain in particular which is appropriate for the patient. Conventional opiates have a good action in the therapy of severe to very severe pain, while their activity on neuropathic pain is unsatisfactory.

The use of inhibitors of the re-uptake of monoamines is limited by side effects, such as e.g. accommodation disorders, serotonin syndrome or QT lengthenings.

SUMMARY OF THE INVENTION

One object of certain embodiments of the present invention is new compounds which are suitable for therapy of depressions, anxiety disorders or pain. These compounds should show as few side effects as possible of the inhibitors of the re-uptake of monoamines, such as, e.g., accommodation disorders, serotonin syndrome or QT lengthenings. Further objects include new active compounds for treatment of anxiety states, urinary incontinence, fibromyalgia, eating disorders, bulimia, hyperactivity, drug dependency, addiction and withdrawal, trichotillomania, Tourette's syndrome, skin diseases, such as postherpetic neuralgia and pruritus, psychoses, memory disorders, cognitive disorders and Alzheimer's disease.

It has now been found that saturated and unsaturated heteroarylcycloalkyl-methyl-amines of the following general formula I inhibit the re-uptake of noradrenaline and/or serotonin. The substances have pronounced antidepressant, anxiolytic and antinociceptive actions and are therefore suitable for treatment of depressions, anxiety disorders and pain. The compounds according to the invention have, in particular, a potential for therapy of states of chronic pain which are accompanied by depressive moods or anxiety disorders. Furthermore, the substances are suitable for treatment of migraine, urinary incontinence, fibromyalgia, eating disorders, bulimia, hyperactivity, drug dependency, addiction and withdrawal, trichotillomania, Tourette's syndrome, skin diseases, such as postherpetic neuralgia and pruritus, psychoses, memory disorders, cognitive disorders and Alzheimer's disease.

The present invention therefore provides saturated and unsaturated heteroarylcycloalkylmethyl-amines of the following general formula I, also in the form of their racemates, enantiomers and diastereomers, in particular mixtures of their enantiomers or diastereomers or an individual enantiomer or diastereomer and their free bases or a salt formed with a physiologically acceptable acid:

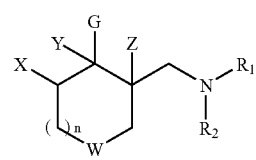

wherein

W is $CH_2$, wherein Y is chosen from H or Cl and at the same time X and Z are H or X and Y together form a bond and Z is H or Y and Z together form a bond and X is H, or W is O, S, SO or $SO_2$, wherein Y is chosen from H, OH or Cl and at the same time X and Z are H or X and Y together form a bond and Z is H or Y and Z together form a bond and X is H, and n=0-3, $R^1$ and $R^2$ independently of one another are chosen from H, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, $NH_2$, SH or OH, $OCH_3$ or unsubstituted; $C_3$-$C_7$-cycloalkyl, saturated or unsaturated, mono- or polysubstituted by F, Cl, Br, I, $NH_2$, SH or OH, $OCH_3$ or unsubstituted, or a corresponding heterocyclic radical in which a C atom in the ring is replaced by S, O or $NR^3$, > where $R^3$ is chosen from
>> H, $C_1$-$C_{10}$-alkyl, $C_2$-$C_{10}$-alkenyl or $C_2$-$C_{10}$-alkynyl, in each case branched or unbranched, mono- or polysubstituted by F, Cl, Br, I, $NH_2$, SH or OH, $OCH_3$ or unsubstituted;
>> alkylaryl, saturated or unsaturated, mono- or polysubstituted by F, Cl, Br, I, $NH_2$, SH or OH, $OCH_3$ or unsubstituted; alkylheteroaryl, saturated or unsaturated, mono- or polysubstituted by F, Cl, Br, I, $NH_2$, SH or OH, $OCH_3$ or unsubstituted, aryl, mono- or polysubstituted by F, Cl, Br, I, $NH_2$, SH or OH, $OCH_3$ or unsubstituted;

or $R^1$ and $R^2$ together form a $C_3$-$C_7$-cycloalkyl, saturated or unsaturated, mono- or polysubstituted by F, Cl, Br, I, $NH_2$, SH or OH, $OCH_3$ or unsubstituted, or a corresponding heterocyclic radical in which a C atom in the ring is replaced by S, O or $NR^4$, > where $R^4$ is chosen from
>> H, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, $NH_2$, SH or OH, $OCH_3$ or unsubstituted, and G is chosen from pyridin-3-yl or pyridin-4-yl. G here can be unsubstituted or mono- or polysubstituted.

In this context, with reference to the radical G, the term "substituted" in the context of this invention is understood as meaning substitution of at least one hydrogen radical by F, Cl, Br, I, CN, $CF_3$, $NO_2$, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, $NH_2$, SH or OH, $OCH_3$ or unsubstituted; $C_3$-$C_7$-cycloalkyl, saturated or unsaturated, mono- or polysubstituted by F, Cl, Br, I, $NH_2$, SH or OH, $OCH_3$ or unsubstituted, or a corresponding heterocyclic radical in which a C atom in the ring is replaced by S, O or $NR^5$, where $R^5$ is chosen from > H, $C_1$-$C_{10}$-alkyl, $C_2$-$C_{10}$-alkenyl or $C_2$-$C_{10}$-alkynyl, in each case branched or unbranched, mono- or polysubstituted by F, Cl, Br, I, $NH_2$, SH or OH, $OCH_3$ or unsubstituted;

$OR^6$, $OC(O)R^6$, $OC(S)R^6$, $C(O)R^6$, $C(O)OR^6$, $C(S)R^6$, $C(S)OR^6$, $SR^6$, $S(O)R^6$ or $S(O_2)R^6$, wherein $R^6$ is chosen from > H, $C_1$-$C_{10}$-alkyl, $C_2$-$C_{10}$-alkenyl or $C_2$-$C_{10}$-alkynyl, in each case branched or unbranched, mono- or polysubstituted by F, Cl, Br, I, $NH_2$, SH or OH, $OCH_3$ or unsubstituted; $C_3$-$C_7$-cycloalkyl, saturated or unsaturated, mono- or polysubstituted by F, Cl, Br, I, $NH_2$, SH or OH, $OCH_3$ or unsubstituted, or a corresponding heterocyclic radical in which a C atom in the ring is replaced by S, O or $NR^7$, where $R^7$ is chosen from
>> H, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, $NH_2$, SH or OH, $OCH_3$ or unsubstituted;
>> alkylaryl, saturated or unsaturated, mono- or polysubstituted by F, Cl, Br, I, $NH_2$, SH or OH, $OCH_3$ or unsubstituted; aryl or heteroaryl, in each case mono- or polysubstituted by F, Cl, Br, I, $NH_2$, SH or OH, $OCH_3$ or unsubstituted;

$NR^8R^9C(O)NR^8R^9$ or $S(O_2)NR^8R^9$, wherein $R^8$ and $R^9$ independently of one another are chosen from > H, $C_1$-$C_{18}$-alkyl, $C_2$-$C_{18}$-alkenyl or $C_3$-$C_{18}$-alkynyl, in each case branched or unbranched, mono- or polysubstituted by F, Cl, Br, I, $NH_2$, SH or OH, $OCH_3$ or unsubstituted; $C_3$-$C_7$-cycloalkyl, saturated or unsaturated, mono- or polysubstituted by F, Cl, Br, I, $NH_2$, SH or OH, $OCH_3$ or unsubstituted, or a corresponding heterocyclic radical in which a C atom in the ring is replaced by S, O or $NR^{10}$, where $R^{10}$ is chosen from
>> H, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, $NH_2$, SH or OH, $OCH_3$ or unsubstituted;
> alkylaryl, saturated or unsaturated, mono- or polysubstituted by F, Cl, Br, I, $NH_2$, SH or OH, $OCH_3$ or unsubstituted; aryl or heteroaryl, in each case mono- or polysubstituted by F, Cl, Br, I, $NH_2$, SH or OH, $OCH_3$ or unsubstituted;

or $R^8$ and $R^9$ together form a $C_3$-$C_7$-cycloalkyl, saturated or unsaturated, mono- or polysubstituted by F, Cl, Br, I, $NH_2$, SH or OH, $OCH_3$ or unsubstituted, or a corresponding heterocyclic radical in which a C atom in the ring is replaced by S, O or $NR^{10}$, where $R^{10}$ is chosen from > H, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, $NH_2$, SH or OH, $OCH_3$ or unsubstituted;

alkylaryl, aryl or heteroaryl, in each case mono- or polysubstituted by F, Cl, Br, I, $NH_2$, SH or OH, $OCH_3$ or unsubstituted.

Preferred compounds are those in which W is $CH_2$, O or S and n=0-3 and $R_1$ and $R_2$ independently of one another are chosen from H, $C_1$-$C_{10}$-alkyl, alkylaryl, saturated or unsaturated, mono- or polysubstituted by F, Cl, Br, I, $NH_2$, SH or OH, $OCH_3$ or unsubstituted; alkylheteroaryl, saturated or unsaturated, mono- or polysubstituted by F, Cl, Br, I, $NH_2$, SH or OH, $OCH_3$ or unsubstituted, or $R_1$ and $R_2$ together form a $C_3$-$C_7$-cycloalkyl, saturated or unsaturated, mono- or polysubstituted by F, Cl, Br, I, $NH_2$, SH or OH, $OCH_3$ or unsubstituted, and the radical G is unsubstituted or substituted by Cl, Br or $OR_6$, wherein $R_6$ is H or $C_1$-$C_{10}$-alkyl In the context of this invention, the term "substituted" which does not refer to the abovementioned definitions for the radical G is understood as meaning substitution of a hydrogen radical by F, Cl, Br, I, $NH_2$, SH or OH, $OCH_3$, where polysubstituted radicals are to be understood as meaning radicals which are substituted several times either on different or on the same atoms, for example three times on the same C atom as in the case of $CF_3$ or at different places as in the case of —CH(OH)—CH=CH—$CHCl_2$.

In the context of this invention, the expression "$C_1$-$C_{10}$-alkyl" denotes hydrocarbons having 1 to 10 carbon atoms.

Examples which may be mentioned are methyl, ethyl, propyl, isopropyl, n-butane, sec-butyl, tert-butyl, n-pentane, neopentyl, n-hexane, n-heptane, n-octane, n-nonane, n-decane, unsubstituted or mono- or polysubstituted.

In the context of this invention, the expression "$C_2$-$C_{10}$-alkenyl" or "$C_2$-$C_{10}$-alkynyl" denotes hydrocarbons having 2 to 10 carbon atoms. Examples which may be mentioned are ethenyl, propenyl, butenyl, pentenyl, hexenyl, heptenyl or octenyl, unsubstituted or mono- or polysubstituted, and ethynyl, propynyl, butynyl, pentynyl, hexynyl, heptynyl or octynyl, mono- or polysubstituted.

In the context of this invention, the expression $C_3$-$C_7$-cycloalkyl denotes cyclic hydrocarbons having 3 to 7 carbon atoms. Examples which may be mentioned are cyclopropyl, cyclobutyl, cyclopentyl, cyclohexyl, cycloheptyl, cyclohexenyl or cycloheptenyl, saturated or unsaturated, unsubstituted or mono- or polysubstituted. In the context of the invention, a "corresponding heterocyclic radical" is understood here as meaning a $C_3$-$C_7$-cycloalkyl in which at least one C atom in the ring is replaced by S, O or N.

Examples which may be mentioned for this are pyrrolidine, pyran, thiolane, piperidine or tetrahydrofuran.

In the context of this invention, the expression "aryl" denotes phenyls or naphthyls.

In the context of this invention, the expression "alkylaryl" denotes aryls substituted by $C_1$-$C_{10}$-alkyls, wherein the expressions aryl and alkyl have the same meaning as above.

In the context of this invention, the expression "heteroaryl" denotes 5- or 6-membered aromatic compounds which are optionally provided with a fused-on aryl system and contain one or two heteroatoms from the group consisting of nitrogen, oxygen and/or sulfur. Examples which may be mentioned in this group are furan, thiophene, pyrrole, pyridine, pyrimidine, quinoline, isoquinoline, phthalazine or quinazoline.

In the context of this invention, the term of salt formed with a physiologically acceptable acid is understood as meaning salts of the particular active compound with inorganic or organic acids which are physiologically acceptable—in particular when used in humans and/or mammals.

The following compounds according to the invention and salts thereof are particularly preferred:

dimethyl-(2-pyridin-3-yl-cyclohex-1-enylmethyl)-amine and the corresponding dihydrochloride (1)

methyl-(2-pyridin-3-yl-cyclohex-1-enylmethyl)-amine and the corresponding hydrochloride (2)

dimethyl-(2-pyridin-3-yl-cyclohex-2-enylmethyl)amine and the corresponding hydrochloride (4)

dimethyl-(2-pyridin-3-yl-cyclohexylmethyl)-amine and the corresponding hydrochloride; diastereoisomer 1 (6)

dimethyl-(2-pyridin-3-yl-cyclohexylmethyl)-amine and the corresponding hydrochloride; diastereoisomer 2 (7)

benzyl-methyl-(2-pyridin-3-yl-cyclohex-1-enylmethyl)-amine and the corresponding hydrochloride (10)

benzyl-methyl-(2-pyridin-3-yl-cyclohex-2-enylmethyl)-amine and the corresponding hydrochloride (11)

[2-chloro-2-(6-chloro-pyridin-3-yl)-cycloheptylmethyl]-dimethyl-amine and the corresponding hydrochloride (13)

(2-chloro-2-pyridin-3-yl-cyclohexylmethyl)-dimethyl-amine and the corresponding hydrochloride (14)

[2-chloro-2-(6-chloro-pyridin-3-yl)-cyclohexylmethyl]-dimethylamine and the corresponding hydrochloride (15)

mixture of [2-(4-bromo-6-chloro-pyridin-3-yl)-cyclohex-1-enylmethyl]-methyl-amine and [2-(4-bromo-6-chloro-pyridin-3-yl)-cyclohex-2-enylmethyl]-methyl-amine and the corresponding hydrochlorides (20)

dimethyl-(2-pyridin-3-yl-cyclohept-1-enylmethyl)-amine and the corresponding hydrochloride (23)

dimethyl-(2-pyridin-3-yl-cyclohept-2-enylmethyl)-amine and the corresponding hydrochloride (24)

mixture of [2-(6-chloro-pyridin-3-yl)-cyclooct-1-enylmethyl]-dimethyl-amine hydrochloride and [2-(6-chloro-pyridin-3-yl)-cyclooct-2-enylmethyl]-dimethyl-amine hydrochloride (25)

dimethyl-(2-pyridin-3-yl-cycloheptylmethyl)-amine and the corresponding hydrochloride; diastereoisomer 1 (26)

dimethyl-(2-pyridin-3-yl-cycloheptylmethyl)-amine and the corresponding hydrochloride; diastereoisomer 2 (27)

dimethyl-(2-pyridin-3-yl-cyclopent-1-enylmethyl)-amine and the corresponding hydrochloride (28)

dimethyl-(2-pyridin-3-yl-cyclopent-2-enylmethyl)-amine and the corresponding hydrochloride (29)

dimethyl-(2-pyridin-3-yl-cyclopentylmethyl)-amine and the corresponding hydrochloride (31)

dimethyl-(2-pyridin-3-yl-cyclooct-1-enylmethyl)-amine and the corresponding hydrochloride (32)

dimethyl-(2-pyridin-3-yl-cyclooct-2-enylmethyl)-amine and the corresponding hydrochloride (33)

dimethyl-(2-pyridin-3-yl-cyclooctylmethyl)-amine and the corresponding hydrochloride (35)

(2-chloro-2-pyridin-4-yl-cycloheptylmethyl)-dimethyl-amine and the corresponding hydrochloride (36)

dimethyl-(2-pyridin-4-yl-cyclohept-2-enylmethyl)-amine and the corresponding hydrochloride (37)

dimethyl-(2-pyridin-4-yl-cyclohept- 1-enylmethyl)-amine and the corresponding hydrochloride (38)

dimethyl-(2-pyridin-4-yl-cyclohex- 1-enylmethyl)-amine and the corresponding hydrochloride (39)

mixture of dimethyl-(2-pyridin-4-yl-cyclohex- 1-enylmethyl)-amine hydrochloride and dimethyl-(2-pyridin-4-yl-cyclohex-2-enylmethyl)-amine hydrochloride (40)

dimethyl-(2-pyridin-4-yl-cyclooct- 1-enylmethyl)-amine and the corresponding hydrochloride (42)

dimethyl-(2-pyridin-4-yl-cyclopent-2-enylmethyl)-amine and the corresponding hydrochloride (43)

dimethyl-(2-pyridin-4-yl-cyclopent-1-enylmethyl)-amine and the corresponding hydrochloride (47)

[2-(6-chloro-pyridin-3-yl)-cyclohept-2-enylmethyl]-dimethyl-amine and the corresponding hydrochloride (48)

[2-(6-chloro-pyridin-3-yl)-cyclohex- 1-enylmethyl] -dimethyl-amine and the corresponding hydrochloride (49)

3-dimethylaminomethyl-4-pyridin-3-yl-tetrahydro-thiopyran-4-ol and the corresponding hydrochloride; diastereoisomer 1 (50)

3-dimethylaminomethyl-4-pyridin-3-yl-tetrahydro-thiopyran-4-ol and the corresponding hydrochloride; diastereoisomer 2 (51)

3-dimethylaminomethyl-4-pyridin-3-yl-tetrahydro-pyran-4-ol and the corresponding hydrochloride (52)

dimethyl-(4-pyridin-3-yl-5,6-dihydro-2H-pyran-3-yl-methyl)-amine and the corresponding hydrochloride (53)

[2-(5-methoxy-pyridin-3-yl)-cyclohex-1-enylmethyl]-dimethyl-amine and the corresponding hydrochloride (54)

[2-(5-methoxy-pyridin-3-yl)-cyclohex-2-enylmethyl]-dimethyl-amine and the corresponding hydrochloride (55)

mixture of [2-(5-methoxy-pyridin-3-yl)-cyclohept-1-enylmethyl]-dimethyl-amine hydrochloride and [2-(5-methoxy-pyridin-3-yl)-cyclohept-2-enylmethyl]-dimethyl-amine hydrochloride (58)

mixture of 5-(2-dimethylaminomethyl-cyclohept-1-enyl)-pyridin-3-ol; hydrochloride and 5-(7-dimethylaminomethyl-cyclohept-1-enyl)-pyridin-3-ol; hydrochloride (59)
[2-(5-methoxy-pyridin-3-yl)-cycloheptylmethyl]-dimethyl-amine and the corresponding hydrochloride (60)
[2-(5-methoxy-pyridin-3-yl)-cyclohexylmethyl]-dimethyl-amine and the corresponding hydrochloride (62)
mixture of [2-(5-methoxy-pyridin-3-yl)-cyclohexylmethyl]-dimethyl-amine (diastereoisomer 1) and [2-(5-methoxy-pyridin-3-yl)-cyclohexylmethyl]-dimethyl-amine (diastereoisomer 2) and the corresponding hydrochlorides (63)
5-(2-dimethylaminomethyl-cyclohex-1-enyl)-pyridin-3-ol and the corresponding hydrochloride (64)
dipropyl-(2-pyridin-3-yl-cyclohex-1-enylmethyl)-amine and the corresponding hydrochloride (65)
dipropyl-(2-pyridin-3-yl-cyclohex-2-enylmethyl)-amine and the corresponding hydrochloride (66)
[2-(5-methoxy-pyridin-3-yl)-cyclooct-1-enylmethyl]-dimethyl-amine hydrochloride and [2-(5-methoxy-pyridin-3-yl)-cyclooct-2-enylmethyl]-dimethyl-amine and the corresponding hydrochlorides (67)
[2-(6-chloro-pyridin-3-yl)-cyclohex-1-enylmethyl]-dimethyl-amine and the corresponding hydrochloride (68)
[2-(6-chloro-pyridin-3-yl)-cyclohex-2-enylmethyl]-dimethyl-amine and the corresponding hydrochloride (69)
[2-(5-methoxy-pyridin-3-yl)-cyclooctylmethyl]-dimethyl-amine and the corresponding hydrochloride; diastereoisomer 1 (70)
[2-(6-chloro-pyridin-3-yl)-cyclooct-2-enylmethyl]-dimethyl-amine and the corresponding hydrochloride (71)
[2-(5-methoxy-pyridin-3-yl)-cyclooctylmethyl]-dimethyl-amine and the corresponding hydrochloride; diastereoisomer 2 (72)
[2-(5-methoxy-pyridin-3-yl)-cyclooct-2-enylmethyl]-dimethyl-amine and the corresponding hydrochloride (73)
[2-(5-methoxy-pyridin-3-yl)-cyclooct-1-enylmethyl]-dimethyl-amine and the corresponding hydrochloride (74)
5-(7-dimethylaminomethyl-cyclohept-1-enyl)-pyridin-3-ol and the corresponding hydrochloride (75)
5-(2-dimethylaminomethyl-cyclohept-1-enyl)-pyridin-3-ol and the corresponding hydrochloride (76)
5-(2-dimethylaminomethyl-cycloheptyl)-pyridin-3-ol and the corresponding hydrochloride (77)
methyl-(2-pyridin-3-yl-cyclohex-2-enylmethyl)-amine and the corresponding hydrochloride (79)

The present invention also provides a process for the preparation of saturated and unsaturated heteroarylcycloalkylmethyl-amines of the abovementioned general formula I. In the following general formula II, A denotes $CH_2$, O, S, SO or $SO_2$.

Heteroarylcycloalkylmethylamines of the general formula I are prepared by a procedure in which cycloalkanones of the general formula II are first reacted with immonium salts of the formula III or with paraformaldehyde and an amine of the formula IV. $R^{10}$ has a meaning the same as $R^1$, $R^{11}$ has a meaning to the same as $R^2$.

The Mannich bases obtained in this way are then reacted with an organometallic compound of the formula V, in which Z denotes lithium and V has a meaning analogous to G. The reaction of the Mannich bases with an organolithium compound of the formula V, in which Z denotes Li and V has a meaning corresponding to G, can be carried out in an aliphatic ether, for example diethyl ether and/or tetrahydrofuran, at temperatures between −70° C. and 60° C. In the case where either $R^{10}$ or $R^{11}$ or both simultaneously are hydrogen, compounds of the general formula III or IV in which $R^{10}$ or $R^{11}$ or $R^{10}$ and $R^{11}$ represent a benzyl radical are employed in the Mannich reaction. This is removed at a suitable point in the reaction sequence by reaction of the corresponding compounds with catalytically activated hydrogen, platinum or palladium absorbed on a support material, such as active charcoal, serving as the catalyst.

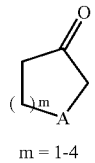

II m = 1-4

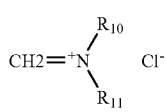

III

NHR10R11

IV

V
|
Z

V

V
|
A

VI

Organolithium compounds of the formula V, in which Z denotes Li and V has a meaning corresponding to G, can be obtained by halogen-lithium exchange by reaction of halogen compounds of the formula VI, in which A denotes Cl, Br or I and V has a meaning corresponding G, with, for example, n-butyllithium/hexane solution. Products of the general formula VII, in which $R^{10}$ has a meaning the same as $R^1$, $R^{11}$ has a meaning the same as $R^2$ and V has a meaning corresponding to G, are first obtained in this way. The compounds of the formula IXb are obtained by reaction of compounds of the general formula VII with thionyl chloride and subsequent working up under basic conditions. In some cases, a mixture of compounds of the general formula VIII, IXa and IXb, in which $R^{10}$ has a meaning the same as $R^1$, $R^{11}$ has a meaning the same as $R^2$ and V has a meaning corresponding to G, occurs. These can be separated by column chromatography or crystallization. Compounds of the general formula IXa can be obtained in a targeted manner by reactions of compounds of the general formula VII with sulfuric acid.

Subsequent hydrogenation of compounds of the general formula IXa or IXb, in which $R^{10}$ has a meaning analogous to $R^1$, $R^{11}$ has a meaning analogous to $R^2$ and V has a meaning corresponding to G, with catalytically activated hydrogen, platinum or palladium absorbed on a support material, such as active charcoal, serving as the catalyst, leads to compounds of the formula X, in which $R^{10}$ has a meaning analogous to $R^1$, $R^{11}$ has a meaning analogous to $R^2$ and V has a meaning corresponding to G. The hydrogenation is carried out in a solvent, such as ethyl acetate or a $C_1$-$C_4$-alkyl alcohol, under pressures of 0.1 to 10 bar and at temperatures of 20° C. to 80° C.

If A is S, these compounds can also be converted into the corresponding SO and $SO_2$ compounds with an oxidizing agent at a suitable point in the reaction sequence.

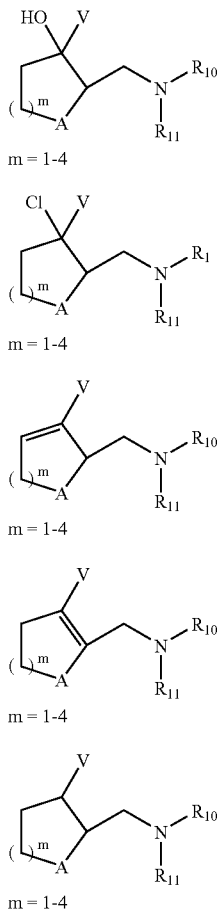

VII m = 1-4

VIII m = 1-4

IXa m = 1-4

IXb m = 1-4

X m = 1-4

Under the reaction conditions mentioned, OH, SH and NH$_2$ groups can undergo undesirable side reactions. It is therefore preferable to provide these with protective groups or, in the case of NH$_2$, to replace this by NO$_2$ and to split off the protective group or reduce the NO$_2$ group in the last reaction step. The invention therefore also provides a modification of the process described above in which at least one OH group contained in formula I is replaced by an OSi(Ph)$_2$tert-but group, at least one SH group is replaced by an S-p-methoxybenzyl group and/or at least one NH$_2$ group is replaced by an NO$_2$ group and, after the entire reaction sequence, an OSi(Ph)$_2$tert-but group is split off with tetrabutylammonium fluoride in tetrahydrofuran and/or at least one p-methoxybenzyl group is split off with a metal amine, preferably sodium amine, and/or at least one NO$_2$ group is reduced to NH$_2$.

Furthermore, carboxylic acid or thiocarboxylic acid groups are not stable under the conditions of the BuLi reaction under certain circumstances, so that it is preferable to react methyl esters thereof and to hydrolyse the process product from the BuLi reaction with KOH solution or NaOH solution in methanol at 40° C.-60° C. in the last reaction step. The invention therefore also provides a modification of the process described above in which, after the BuLi reaction, a process product having at least one C(O)OCH$_3$ and/or C(S)OCH$_3$ group is hydrolysed with KOH solution or NaOH solution in methanol at 40° C.-60° C.

The purification of the compounds obtained in the individual reaction sequences is carried out by crystallization or column chromatography.

The compounds of the formula I can be converted with physiologically acceptable acids, such as hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid, into their salts in a manner known per se. Preferably, the salt formation is carried out in a solvent, such as diisopropyl ether, acetic acid alkyl esters, acetone and/or 2-butanone. Trimethylchlorosilane in aqueous solution is particularly suitable for the preparation of the hydrochlorides.

The saturated and unsaturated heteroarylcycloalkylmethyl-amines of the general formula I according to the invention are toxicologically acceptable and are therefore suitable as pharmaceutical active compounds in pharmaceutical formulations.

The present invention therefore also provides pharmaceutical formulations which comprise at least one compound of the general formula I according to the invention and optionally physiologically acceptable auxiliary substances. The pharmaceutical formulations according to the invention are preferably suitable for combating pain (in particular chronic pain, neuropathic pain, inflammatory pain), migraine and fibromyalgia or for treatment of depressions (unipolar, severe depression with and without madness, moderate depressions, mild depressions, melancholy, bipolar depressions; bipolar diseases I (mania and severe depressions), bipolar diseases II (hypomania and severe depressions), cyclothymic personality disorders (hypomania and mild depressions), subtypes), anxiety states (subtypes generalized anxiety disorders, panic attacks, obsessive syndromes, social anxiety disorder, phobias, PTSD), sleep disorders, urinary incontinence (stress and urgency), eating disorders, bulimia, attention deficit hyperactivity disorder, addiction and dependency, trichotillomania, neuroleptic agent and memory disorders.

The present invention also provides the use of at least one compound of the general formula I for the preparation of a pharmaceutical formulation for combating pain (in particular chronic pain, neuropathic pain, inflammatory pain), migraine and fibromyalgia or for treatment of depressions (unipolar, severe depression with and without madness, moderate depressions, mild depressions, melancholy, bipolar depressions; bipolar diseases I (mania and severe depressions), bipolar diseases II (hypomania and severe depressions), cyclothymic personality disorders (hypomania and mild depressions), subtypes), anxiety states (subtypes generalized anxiety disorders, panic attacks, obsessive syndromes, social anxiety disorder, phobias, PTSD), sleep disorders, urinary incontinence (stress and urgency), eating disorders, bulimia, attention deficit hyperactivity disorder, addiction and dependency, trichotillomania, neuroleptic agent and memory disorders.

The pharmaceutical formulations according to the invention can be in the form of liquid, semi-solid or solid pharmaceutical formulation forms, for example in the form of injection solutions, drops, juices, syrups, sprays, suspensions, tablets, patches, capsules, plasters, suppositories, ointments, creams, lotions, gels, emulsions or aerosols, or in multiparticulate form, for example in the form of pellets or granules, and can also be administered as such.

In addition to at least one compound of the general formula I according to the invention, the pharmaceutical formulations according to the invention conventionally comprise further physiologically acceptable pharmaceutical auxiliary substances, which are preferably chosen from the group consisting of carrier materials, fillers, solvents, diluents, surface-active substances, dyestuffs, preservatives, disintegrating agents, slip agents, lubricants, flavourings and binders.

The choice of the physiologically acceptable auxiliary substances and the amounts thereof to be employed depends on whether the pharmaceutical formulation is to be administered orally, subcutaneously, parenterally, intravenously, intraperitoneally, intradermally, intramuscularly, intranasally, buccally, rectally or locally, for example on infections on the skin, the mucous membranes and on the eyes. Formulations in the form of tablets, coated tablets, capsules, granules, pellets, drops, juices and syrups are preferably suitable for oral administration, and solutions, suspensions, easily reconstitutable dry formulations and sprays are suitable for parenteral, topical and inhalatory administration. Compounds of the general formula I according to the invention in a depot in dissolved form or in a plaster, optionally with the addition of agents which promote penetration through the skin, are suitable formulations for percutaneous administration. Formulation forms which can be used orally or percutaneously can also release the compounds of the general formula I in a delayed manner.

The pharmaceutical formulations according to the invention can be prepared with the aid of conventional agents, devices, methods and processes known to the expert, such as are described, for example, in "Remington's Pharmaceutical Sciences", ed. A. R. Gennaro, 17th ed., Mack Publishing Company, Easton, Pa. (1985), in particular in part 8, section 76 to 93. The corresponding description in the literature is introduced herewith as reference and forms part of the disclosure.

The amount of the particular saturated or unsaturated heteroarylcycloalkylmethyl-amines of the general formula I according to the invention to be administered to the patient can vary and depends, for example, on the weight or the age of the patient and on the mode of administration, the indication and the severity of the disease. 0.005 to 500 mg/kg, preferably 0.05 to 5 mg/kg of body weight of the patient of at least one compound of the general formula I according to the invention are conventionally administered.

The invention also relates to a method for treatment of depressions, anxiety disorders and/or pain, in which the compounds used according to the invention are used.

EXAMPLES

For simplicity and illustrative purposes, the principles of the present invention are described by referring to various examples. The invention is not limited in its application to the details of any particular formulation shown, since the invention is capable of other embodiments. The following examples are provided for illustrative purposes and do not and should not be understood to limit the claims appended hereto. The terminology used herein is for the purpose of description and not of limitation.

In these examples, the following generally applies:
The yields of the compounds prepared are not optimized.
All temperatures are uncorrected.
Silica gel 60 (0.040-0.063 mm) from E. Merck, Darmstadt was employed as the stationary phase for the column chromatography.
The thin layer chromatography investigations were carried out with HPTLC precoated plates, silica gel 60 F 254 from E. Merck, Darmstadt.
The mixing ratios of the mobile phases for all the chromatography analyses are always stated in volume/volume.
Ether means diethyl ether.
Unless stated otherwise, petroleum ether having the boiling range of 50° C.-70° C. was used.

Example 1

Dimethyl-(2-pyridin-3-yl-cyclohex-1-enylmethyl) amine dihydrochloride 224 ml n-butyllithium solution (2.5 mol/l in hexane) were added dropwise to a solution of 54 ml 3-bromopyridine in 750 ml analytical grade diethyl ether in the course of 30 minutes at a temperature of −35 to −40° C. After a further 20 minutes at this temperature, 86.9 g 2-dimethylaminomethylcyclohexanone, dissolved in 90 ml analytical grade diethyl ether, were added dropwise in the course of 30 minutes, with continued cooling, and the mixture was stirred again for 60 minutes with gentle warming to −30° C. 150 ml water were then added with warming of the reaction mixture to 0° C., the phases were separated, the aqueous phase was extracted twice with ethyl acetate, the combined organic phases were dried over magnesium sulfate and filtered and the filtrate was concentrated. The crude product obtained (139 g) was dissolved in 700 ml absolute ethanol, and 142 ml chlorotrimethylsilane and 20.2 ml water were added in succession and the mixture was stirred in an ice-bath for 12 hours. The solid which had precipitated out was filtered off with suction, washed with a little absolute ethanol and dried at 90° C. in vacuo (approx. 50 mbar) for two hours. 63.9 g 2-dimethylaminomethyl-1-pyridin-3-yl-cyclohexanol hydrochloride were obtained.

129 ml thionyl chloride were added dropwise to 74.9 g 2-dimethylaminomethyl-1-pyridin-3-yl-cyclohexanol hydrochloride with vigorous evolution of gas, and the mixture was heated at 60 to 65° C. for 2.5 hours, while stirring, and was then concentrated under a water pump. After cooling, first 200 ml water and then 100 ml sodium hydroxide solution (32 per cent strength by weight) were added, the mixture was then extracted twice with 250 ml of a mixture of equal volumes of tetrahydrofuran and ethyl acetate each time, the combined extracts were dried over magnesium sulfate and filtered and the filtrate was concentrated. The crude product obtained (48.9 g) was dissolved in 350 ml absolute ethanol, and 57.4 ml chlorotrimethylsilane and 8.1 ml water were added in succession and the mixture was stirred in an ice-bath for 12 hours. The solid which had precipitated out was filtered off with suction, washed with a little absolute ethanol and dried at 90° C. in vacuo (approx. 50 mbar) for two hours. 34.7 g of crude dimethyl-(2-pyridin-3-yl-cyclohex-1-enylmethyl) amine dihydrochloride were obtained. For final purification, 168 g of crude dimethyl-(2-pyridin-3-yl-cyclohex- 1-enylmethyl)amine dihydrochloride prepared according to the above instructions were dissolved in 650 ml of boiling absolute ethanol and crystallized again by cooling in an ice-bath, while stirring. After the crystals had been stirred overnight at room temperature, they were filtered off with suction, washed with a little absolute ethanol and dried at 120° C. in vacuo (approx. 50 mbar) for 4.5 hours. 121 g dimethyl-(2-pyridin-3-yl-cyclohex- 1-enylmethyl)amine dihydrochloride with a melting point of 215 to 218° C. were obtained.

The following were prepared analogously to Example 1:

Example 23

Dimethyl-(2-pyridin-3-yl-cyclohept-1-enylmethyl)-amine hydrochloride

Example 28

Dimethyl-(2-pyridin-3-yl-cyclopent-1-enylmethyl)-amine hydrochloride

Example 32

Dimethyl-(2-pyridin-3-yl-cyclooct-1-enylmethyl)-amine hydrochloride

Example 38

Dimethyl-(2-pyridin-4-yl-cyclohept-1-enylmethyl)-amine hydrochloride

Example 39

Dimethyl-(2-pyridin-4-yl-cyclohex-1-enylmethyl)-amine hydrochloride

Example 42

Dimethyl-(2-pyridin-4-yl-cyclooct-1-enylmethyl)-amine hydrochloride

Example 47

Dimethyl-(2-pyridin-4-yl-cyclopent-1-enylmethyl)-amine hydrochloride

Example 54

[2-(5-Methoxy-pyridin-3-yl)-cyclohex-1-enylmethyl]-dimethyl-amine hydrochloride

Example 64

5-(2-Dimethylaminomethyl-cyclohex-1-enyl)-pyridin-3-ol hydrochloride

Example 65

Dipropyl-(2-pyridin-3-yl-cyclohex-1-enylmethyl)-amine hydrochloride

Example 68

[2-(6-Chloro-pyridin-3-yl)-cyclohex-1-enylmethyl]-dimethyl-amine hydrochloride

Example 74

[2-(5-Methoxy-pyridin-3-yl)-cyclooct-1-enylmethyl]-dimethyl-amine hydrochloride

Example 76

5-(2-Dimethylaminomethyl-cyclohept-1-enyl)-pyridin-3-ol hydrochloride.

Regioisomeric olefins were in some cases also obtained in the preparation of the abovementioned compounds:

Example 20

Mixture of [2-(4-bromo-6-chloro-pyridin-3-yl)-cyclohex-1-enylmethyl]-methyl-amine hydrochloride and [2-(4-bromo-6-chloro-pyridin-3-yl)-cyclohex-2-enylmethyl]-methyl-amine hydrochloride

Example 25

Mixture of [2-(6-chloro-pyridin-3-yl)-cyclooct-1-enylmethyl]-dimethyl-amine hydrochloride and [2-(6-chloro-pyridin-3-yl)-cyclooct-2-enylmethyl]-dimethyl-amine hydrochloride

Example 40

Mixture of dimethyl-(2-pyridin-4-yl-cyclohex-1-enylmethyl)-amine hydrochloride and dimethyl-(2-pyridin-4-yl-cyclohex-2-enylmethyl)-amine hydrochloride

Example 58

Mixture of [2-(5-methoxy-pyridin-3-yl)-cyclohept-1-enylmethyl]-dimethyl-amine hydrochloride and [2-(5-methoxy-pyridin-3-yl)-cyclohept-2-enylmethyl]-dimethyl-amine hydrochloride

Example 59

Mixture of 5-(2-dimethylaminomethyl-cyclohept-1-enyl)-pyridin-3-ol; hydrochloride and 5-(7-dimethylaminomethyl-cyclohept-1-enyl)-pyridin-3-ol; hydrochloride

Example 67

Mixture of [2-(5-methoxy-pyridin-3-yl)-cyclooct-1-enylmethyl]-dimethyl-amine hydrochloride and [2-(5-methoxy-pyridin-3-yl)-cyclooct-2-enylmethyl]-dimethyl-amine hydrochloride In addition to the olefins, the following chlorinated derivatives, which were separated off from the olefins by column chromatography, were also obtained for the following examples by the procedure described in Example 1:

Example 13

[2-Chloro-2-(6-chloro-pyridin-3-yl)-cycloheptylmethyl]-dimethyl-amine hydrochloride

Example 14

(2-Chloro-2-pyridin-3-yl-cyclohexylmethyl)-dimethyl-amine hydrochloride

Example 15

[2-Chloro-2-(6-chloro-pyridin-3-yl)-cyclohexylmethyl]-dimethyl-amine hydrochloride

Example 36

(2-Chloro-2-pyridin-4-yl-cycloheptylmethyl)-dimethyl-amine hydrochloride.

Example 2

Methyl-(2-pyridin-3-yl-cyclohex-1-enylmethyl)amine hydrochloride 37.6 ml cyclohexanone, 5.75 g paraformaldehyde, 38 ml glacial acetic acid and 30.2 g benzylmethylamine hydrochloride were heated at 105° C. (bath temperature) for 25 minutes, while stirring, the mixture was concentrated in vacuo (10 mbar), the residue was taken up in 100 ml 2-butanone and the mixture was concentrated again in vacuo. The residue was heated under reflux with 150 ml 2-butanone. After cooling to room temperature, the mixture was filtered and the residue on the filter was dried in vacuo. 36 g 2-[(benzylmethylamino)methyl]cyclohexanone were obtained.

50 ml n-butyllithium solution (2.5 mol/l in hexane) were added dropwise to a solution of 12.1 ml 3-bromopyridine in 180 ml analytical grade diethyl ether at a temperature of −45 to −50° C. in the course of 30 minutes. After a further 20 minutes at this temperature, 25.2 g 2-[(benzylmethylamino)methyl]cyclohexanone, dissolved in 50 ml analytical grade diethyl ether, were added dropwise in the course of 30 minutes, with continued cooling, and the mixture was subsequently stirred for a further 60 minutes. The cooling was then removed and 54 ml water were added, while warming the reaction mixture from −20 to 0° C., the phases were separated, the aqueous phase was extracted twice with a mixture of equal volumes of tetrahydrofuran and ethyl acetate, the combined organic phases were dried over magnesium sulfate and filtered and the filtrate was concentrated. The crude product obtained (33.0 g) was chromatographed on silica gel first with acetone/ethyl acetate (V:V=1:2) and then again with pure ethyl acetate, the product fraction obtained (23.6 g) was dissolved in 230 ml ethyl acetate, and 2.74 ml water and 19.3 ml chlorotrimethylsilane were added and the mixture, from which an oil settled out, was concentrated to dryness. The residue was taken up in 90 ml water and 17.9 ml sodium hydroxide solution (32 percent strength by weight), the mixture was extracted twice with 90 ml ethyl acetate each time, the combined extracts were dried over magnesium sulfate and filtered and the filtrate was concentrated. 23.6 g of crude product were again obtained, to which, after dissolving in 230 ml acetone, 2.74 ml water and 19.3 ml chlorotrimethylsilane, dissolved in 100 ml acetone, were added. The supernatant was decanted off from the solid formed and the residue was heated to 50° C. with 230 ml acetone. After cooling, the supernatant was decanted off again and the residue was dried in vacuo (50 mbar) at 50° C. 28.8 g 2-[(benzylmethylamino)methyl]-1-pyridin-3-yl-cyclohexanol hydrochloride were obtained.

11.1 g 2-[(benzylmethylamino)methyl]-1-pyridin-3-yl-cyclohexanol hydrochloride were dissolved in 110 ml glacial acetic acid under nitrogen, 2.0 g palladium-on-active charcoal (10 percent by weight) were added as a catalyst and the mixture was stirred under a hydrogen pressure of 2.0 bar until the uptake of hydrogen had ended. The mixture was filtered with suction, the filtrate was concentrated, the residue was stirred overnight with 75 ml isopropanol and the precipitate obtained was filtered off with suction and dried. 6.18 g 2-methylaminomethyl-1-pyridin-3-yl-cyclohexanol hydrochloride were obtained.

26 ml thionyl chloride were added dropwise to 5.20 g 2-methylaminomethyl-1-pyridin-3-yl-cyclohexanol hydrochloride and the mixture was heated (bath temperature 65 °C) for 90 minutes, while stirring, and then concentrated under a water pump. After cooling, dilute sodium hydroxide solution (2 mol/l) was added, the mixture was extracted repeatedly with a mixture of equal volumes of tetrahydrofuran and ethyl acetate, the combined extracts were dried over magnesium sulfate and filtered and the filtrate was concentrated. The crude product obtained (3.25 g) was dissolved in 25 ml absolute ethanol and 8 ml ethyl acetate, and 4.1 ml chlorotrimethylsilane and 0.58 ml water were added in succession. The solid which had precipitated out (1.84 g) was filtered off with suction (cf. Example 79), the mother liquor was rendered basic with dilute sodium hydroxide solution (2 mol/l) and extracted repeatedly with a mixture of equal volumes of tetrahydrofuran and ethyl acetate, the combined extracts were dried over magnesium sulfate and filtered and the filtrate was concentrated. The residue obtained (1.45 g) was chromatographed on silica gel with methanol, to which 0.05 percent by volume of aqueous ammonia solution (25 percent strength by weight) had been added. The product fraction (0.52 g) was dissolved in 50 ml ethyl acetate, and 0.66 ml chlorotrimethylsilane, followed by 92 µl water, were added. 0.57 g methyl-(2-pyridin-3-yl-cyclohex-1-enylmethyl)amine hydrochloride was obtained as a precipitate.

Example 79

Methyl-(2-pyridin-3-yl-cyclohex-2-enylmethyl)amine hydrochloride 1.84 g methyl-(2-pyridin-3-yl-cyclohex-2-enylmethyl)amine were obtained as described for Example 2, and, as described there, were converted into the corresponding hydrochloride in acetone with water and chlorotrimethylsilane.

Example 4

Dimethyl-(2-pyridin-3-yl-cyclohex-2-enylmethyl)amine hydrochloride 224 ml n-butyllithium solution (2.5 mol/l in hexane) were added dropwise to a solution of 54 ml 3-bromopyridine in 750 ml analytical grade diethyl ether in the course of 30 minutes at a temperature of −35 to −40° C. After a further 20 minutes at this temperature, 86.9 g 2-dimethylaminomethylcyclohexanone, dissolved in 90 ml analytical grade diethyl ether, were added dropwise in the course of 30 minutes, with continued cooling, and the mixture was stirred again for 60 minutes with gentle warming to −30° C. 150 ml water were then added with warming of the reaction mixture to 0° C., the phases were separated, the aqueous phase was extracted twice with ethyl acetate, the combined organic phases were dried over magnesium sulfate and filtered and the filtrate was concentrated. The crude product obtained (139 g) was dissolved in 700 ml absolute ethanol, and 142 ml chlorotrimethylsilane and 20.2 ml water were added in succession and the mixture was stirred in an ice-bath for 12 hours. The solid which had precipitated out was filtered off with suction, washed with a little absolute ethanol and dried at 90° C. in vacuo (approx. 50 mbar) for two hours. 63.9 g 2-dimethylaminomethyl-1-pyridin-3-yl-cyclohexanol hydrochloride were obtained.

40 ml 96% strength sulfuric acid were added to 7.8 g dimethylaminomethyl-1-pyridin-3-yl-cyclohexanol hydrochloride, while cooling with ice. When the evolution of gas had ended, the mixture was stirred at room temperature for 45 minutes. The solution was subsequently poured on to approx. 400 g of crushed ice. It was then rendered alkaline by addition of sodium hydroxide lozenges, while cooling with ice, and the mixture was extracted 3× with a total of 600 ml ethyl acetate. The combined organic phases were dried over magnesium sulfate and evaporated to dryness on a rotary evaporator in vacuo at 50° C. 4.2 g dimethyl-(2-pyridin-3-yl-cyclohex-2-enylmethyl)amine hydrochloride were obtained in this way.

The following were prepared analogously:

Example 24

Dimethyl-(2-pyridin-3-yl-cyclohept-2-enylmethyl)-amine hydrochloride

Example 29

Dimethyl-(2-pyridin-3-yl-cyclopent-2-enylmethyl)-amine hydrochloride

Example 33

Dimethyl-(2-pyridin-3-yl-cyclooct-2-enylmethyl)-amine hydrochloride

Example 37

Dimethyl-(2-pyridin-4-yl-cyclohept-2-enylmethyl)-amine hydrochloride

Example 43

Dimethyl-(2-pyridin-4-yl-cyclopent-2-enylmethyl)-amine hydrochloride

Example 48

[2-(6-chloro-pyridin-3-yl)-cyclohept-2-enylmethyl]-dimethyl-amine hydrochloride

Example 49

[2-(6-Chloro-pyridin-3-yl)-cyclohex-1-enylmethyl]-dimethyl-amine hydrochloride

Example 55

[2-(5-Methoxy-pyridin-3-yl)-cyclohex-2-enylmethyl]-dimethyl-amine hydrochloride

Example 66

Dipropyl-(2-pyridin-3-yl-cyclohex-2-enylmethyl)-amine hydrochloride

Example 69

[2-(6-Chloro-pyridin-3-yl)-cyclohex-2-enylmethyl]-dimethyl-amine hydrochloride

Example 71

[2-(6-Chloro-pyridin-3-yl)-cyclooct-2-enylmethyl]-dimethyl-amine hydrochloride

Example 73

[2-(5-Methoxy-pyridin-3-yl)-cyclooct-2-enylmethyl]-dimethyl-amine hydrochloride

Example 75

5-(7-dimethylaminomethyl-cyclohept-1-enyl)-pyridin-3-ol hydrochloride.

Example 6 cis-Dimethyl-(2-pyridin-3-yl-cyclohexylmethyl) amine hydrochloride 6.90 g dimethyl-(2-pyridin-3-yl-cyclohex-2-enylmethyl) amine hydrochloride were dissolved in 70 ml methanol and hydrogenated in the presence of 1.04 g palladium-on-active charcoal (10 percent by weight) for five hours under a hydrogen pressure of 2 bar. The mixture was then filtered, the filtrate was concentrated in vacuo, the residue was converted into the base with two molar sodium hydroxide solution and a mixture of equal volumes of ethyl acetate and tetrahydrofuran and the base was extracted with ethyl acetate. After drying and concentration, the residue (4.47 g) was chromatographed on silica gel with a mixture of equal volumes of methanol, ethyl acetate and n-hexane. The main fraction (3.72 g) was dissolved in approx. 40 ml acetone/ethanol (V/V=9:1), and half a molar equivalent of water and one molar equivalent of chlorotrimethylsilane were added. After the mixture had been stirred overnight, it was concentrated to dryness, the residue was treated in an ultrasonic bath with 72 ml THF and 18 ml ethanol for 30 minutes, the suspension was stirred overnight and filtered with suction and the residue was dried. 2.42 g cis-dimethyl-(2-pyridin-3-yl-cyclohexylmethyl)amine hydrochloride with a melting point of 219-222° C. were obtained.

Example 7 trans-Dimethyl-(2-pyridin-3-yl-cyclohexylmethyl) amine hydrochloride 224 ml n-butyllithium solution (2.5 mol/l in hexane) were added dropwise to a solution of 54 ml 3-bromopyridine in 750 ml analytical grade diethyl ether in the course of 30 minutes at a temperature of −35 to −40° C. After a further 20 minutes at this temperature, 86.9 g 2-dimethylaminomethylcyclohexanone, dissolved in 90 ml analytical grade diethyl ether, were added dropwise in the course of 30 minutes, with continued cooling, and the mixture was stirred again for 60 minutes with gentle warming to −30° C. 150 ml water were then added with warming of the reaction mixture to 0° C., the phases were separated, the aqueous phase was extracted twice with ethyl acetate, the combined organic phases were dried over magnesium sulfate and filtered and the filtrate was concentrated. The crude product obtained (139 g) was dissolved in 700 ml absolute ethanol, and 142 ml chlorotrimethylsilane and 20.2 ml water were added in succession and the mixture was stirred in an ice-bath for 12 hours. The solid which had precipitated out was filtered off with suction, washed with a little absolute ethanol and dried at 90° C. in vacuo (approx. 50 mbar) for two hours. 63.9 g 2-dimethylaminomethyl-1-pyridin-3-yl-cyclohexanol hydrochloride were obtained.

40 ml 96% strength sulfuric acid were added to 7.8 g dimethylaminomethyl-1-pyridin-3-yl-cyclohexanol hydrochloride, while cooling with ice. When the evolution of gas had ended, the mixture was stirred at room temperature for 45 minutes. The solution was subsequently poured on to approx. 400 g of crushed ice. It was then rendered alkaline by addition of sodium hydroxide lozenges, while cooling with ice, and the mixture was extracted 3× with a total of 600 ml ethyl acetate. The combined organic phases were dried over magnesium sulfate and evaporated to dryness on a rotary evaporator in vacuo at 50° C. 4.2 g of the title compound were obtained in this way.

3.0 g dimethyl-(2-pyridin-3-yl-cyclohex-2-enylmethyl)-amine hydrochloride were dissolved in ethanol (100 ml), and palladium-on-charcoal (10% Pd, 300 mg) was then added. The suspension was hydrogenated with hydrogen (0.82 l) under a pressure of 4 bar for 4 hours. The catalyst was then separated off by filtration and the solvent was distilled off on a rotary evaporator. 3.1 g of a white hygroscopic solid were obtained.

The crude product was converted into the base by rendering alkaline with sodium hydroxide solution and subsequent extraction with ethyl acetate. It was then chromatographed twice on silica gel (diisopropyl ether:methanol:ammonia=300:150:1 and acetonitrile:ethanol:ammonia=200:100:1). The crude product obtained (70 mg) was dissolved in ethyl acetate (20 ml). Trimethylchlorosilane (0.08 ml; 0.63 mmol) and water (0.01 ml; 0.55 mmol) were then added, while cooling with ice, and the mixture was subsequently stirred for 30 minutes. After filtration, dimethyl-(2-pyridin-3-yl-cyclohexylmethyl)-amine hydrochloride (0.09 g) was obtained as a white solid.

The following were prepared analogously to Example 7:

Example 26 cis-Dimethyl-(2-pyridin-3-yl-cycloheptylmethyl)-amine hydrochloride

Example 27 trans-Dimethyl-(2-pyridin-3-yl-cycloheptylmethyl)-amine hydrochloride

Example 31

Dimethyl-(2-pyridin-3-yl-cyclopentylmethyl)-amine hydrochloride

Example 35

Dimethyl-(2-pyridin-3-yl-cyclooctylmethyl)-amine hydrochloride

Example 60

[2-(5-Methoxy-pyridin-3-yl)-cycloheptylmethyl]-dimethyl-amine hydrochloride

Example 62

[2-(5-Methoxy-pyridin-3-yl)-cyclohexylmethyl]-dimethyl-amine hydrochloride

Example 63

Mixture of cis-[2-(5-methoxy-pyridin-3-yl)-cyclohexylmethyl]-dimethyl-amine hydrochloride and trans-[2-(5-methoxy-pyridin-3-yl)-cyclohexylmethyl]-dimethyl-amine hydrochloride

Example 70 trans-[2-(5-Methoxy-pyridin-3-yl)-cyclooctylmethyl]-dimethyl-amine and the corresponding hydrochloride

Example 72 cis-[2-(5-Methoxy-pyridin-3-yl)-cyclooctylmethyl]-dimethyl-amine hydrochloride

Example 77

5-(2-Dimethylaminomethyl-cycloheptyl)-pyridin-3-ol hydrochloride.

Example 10

Benzylmethyl-(2-pyridin-3-yl-cyclohex-1-enylmethyl)amine hydrochloride 5.5 g 2-[(benzylmethylamino)methyl]-1-pyridin-3-ylcyclohexanol hydrochloride and 27.5 ml thionyl chloride were heated at a bath temperature of 75° C. for one hour. After the mixture had been concentrated in vacuo, the residue was taken up in ethyl acetate and sodium hydroxide solution (32 percent strength by weight) and the organic phase was separated off, dried and concentrated. The crude product obtained (3.7 g) was chromatographed on silica gel with diisopropyl ether/ethyl acetate (V/V=2:1). 1.23 g benzylmethyl-(2-pyridin-3-ylcyclohex-1-enylmethyl)amine were obtained, and were dissolved in approx. 25 ml acetone and converted into the corresponding hydrochloride with 1.66 µl water and 1.18 ml chlorotrimethylsilane.

Example 11

Benzylmethyl-(2-pyridin-3-yl-cyclohex-2-enylmethyl)amine hydrochloride 1.37 g benzylmethyl-(2-pyridin-3-yl-cyclohex-2-enylmethyl)amine hydrochloride were also obtained as described for Example 10 and were dissolved in approx. 30 ml acetone and converted into the corresponding hydrochloride with 1.86 µl water and 1.30 ml chlorotrimethylsilane.

Example 50 cis-3-Dimethylaminomethyl-4-pyridin-3-yl-tetrahydrothiopyran-4-ol hydrochloride 5.00 g tetrahydrothiopyran-4-one were dissolved in 15 ml acetonitrile, and 4.03 g N,N-dimethyl-methylenammonium chloride, followed by 40 µl acetyl chloride, were added. After the mixture had been stirred at a bath temperature of 60° C. for 45 minutes, it was stirred at room temperature for 60 hours and the precipitate formed was filtered off with suction and dried. 8.17 g 3-dimethylaminomethyl-tetrahydrothiopyran-4-one hydrochloride with a melting point of 155-157° C. were obtained. The corresponding base was liberated from this with methylene chloride and sodium hydroxide solution (32 percent strength by weight).

31 ml n-butyllithium solution (2.5 mol/l in hexane) were added dropwise to a solution of 7.5 ml 3-bromopyridine in 110 ml analytical grade diethyl ether in the course of 15 minutes at a temperature of −40 to −45° C. After a further 60 minutes at −50° C., 10.8 g 3-dimethylaminomethyl-tetrahydrothiopyran-4-one, dissolved in 45 ml analytical grade diethyl ether, were added dropwise in the course of 15 minutes, with continued cooling, and the mixture was stirred overnight, while warming to room temperature. 25 ml water were added at approx. 15° C., the phases were separated, the aqueous phase was extracted twice with diethyl ether, the combined organic phases were dried over magnesium sulfate and filtered and the filtrate was concentrated. The crude product obtained (15.0 g) was chromatographed on silica gel with a mixture of equal volumes of methanol, ethyl acetate and n-hexane. The main fraction (7.83 g) was dissolved in approx. 80 ml ethanol and converted into the hydrochloride of cis-3-dimethylaminomethyl-4-pyridin-3-yl-tetrahydrothiopyran-4-ol with a melting point of 262-263° C. with 2.2 molar equivalents of chlorotrimethylsilane and water.

Example 51 trans-3-Dimethylaminomethyl-4-pyridin-3-yl-tetrahydrothiopyran-4-ol hydrochloride As described for Example 50, 1.03 g of the polar diastereoisomer trans-3-dimethylaminomethyl-4-pyridin-3-yltetrahydrothiopyran-4-ol hydrochloride were also obtained as a by-product during the column chromatography, and were converted into the corresponding hydrochloride in an analogous manner.

Example 52 cis-3-Dimethylaminomethyl-4-pyridin-3-yl-tetrahydropyran-4-ol hydrochloride 9.6 g tetrahydropyran-4-one were dissolved in 29 ml acetonitrile, and 9.69 g N,N-dimethyl-methylenammonium chloride, followed by 100 μl acetyl chloride, were added. After the mixture had been stirred at a bath temperature of 60° C. for 45 minutes, it was stirred at room temperature for 60 hours and the precipitate formed was filtered off with suction and dried. 16.4 g 3-dimethylaminomethyltetrahydropyran-4-one hydrochloride were obtained. The corresponding base was liberated from this with methylene chloride and sodium hydroxide solution (32 percent strength by weight).

35 ml n-butyllithium solution (2.5 mol/l in hexane) were added dropwise to a solution of 8.4 ml 3-bromopyridine in 125 ml analytical grade diethyl ether in the course of 15 minutes at a temperature of −40 to −45° C. After a further 60 minutes at −50° C., 8.7 g 3-dimethylaminomethyl-tetrahydropyran-4-one, dissolved in 45 ml analytical grade diethyl ether, were added dropwise in the course of 15 minutes, with continued cooling, and the mixture was stirred overnight, while warming to room temperature. 28 ml water were added at approx. 15° C., the phases were separated, the aqueous phase was extracted twice with diethyl ether, the combined organic phases were dried over magnesium sulfate and filtered and the filtrate was concentrated. The crude product obtained (13.5 g) was chromatographed on silica gel with a mixture of equal volumes of methanol and methylene chloride. In addition to a small amount (1.5 g) of the polar trans-diastereoisomer, the main fraction (3.70 g) was dissolved in approx. 40 ml ethanol and converted into the hydrochloride of cis-3-dimethylaminomethyl-4-pyridin-3-yltetrahydropyran-4-ol with a melting point of 276-277° C. with 2.2 molar equivalents of chlorotrimethylsilane and water.

Example 53

Dimethyl-(4-pyridin-3-yl-5,6-dihydro-2H-pyran-3-yl-methyl)amine hydrochloride 4.95 g of a mixture of cis- and trans-3-dimethylaminomethyl-4-pyridin-3-yl-tetrahydropyran-4-ol hydrochloride and 6.6 ml thionyl chloride were stirred at a bath temperature of 65° C. for two hours and then overnight at room temperature. After the mixture had been concentrated in vacuo, the residue was taken up in ethyl acetate and sodium hydroxide solution (32 percent strength by weight) and the organic phase was separated off, dried and concentrated. The crude product obtained (2.2 g) was chromatographed on silica gel with a mixture of equal volumes of methanol and methylene chloride. In addition to 0.82 g of the target product, a mixed fraction of 1.26 g was obtained, which was chromatographed again under analogous conditions. A total of 0.96 g of the target product was obtained in this way, and was dissolved in approx. 10 ml ethanol and converted into the corresponding hydrochloride of dimethyl-(4-pyridin-3-yl-5,6-dihydro-2H-pyran-3-yl-methyl)amine with a melting point of 244-248° C. with 0.18 ml water and 1.23 ml chlorotrimethylsilane.

Pharmacological Investigations a) Investigations of the Inhibition of the Re-uptake of 5-HT and NA In order to be able to carry out these in vitro studies, synaptosomes are freshly isolated from rat brain areas. In each case a so-called "$P_2$" fraction is used, which is prepared exactly in accordance with the instructions of Gray, E. G. and Whittaker, V. P. (1962, J. Anat. 76, 79-88). These vesicular particles are isolated from the hypothalamus for the NA re-uptake and from the medulla +pons region of male rat brains for the 5-HT re-uptake.

The following characteristic data were determined for the NA and 5-HT re-uptake:

NA re-uptake: Km=0.32±0.11 μM

5-HT re-uptake: Km=0.084±0.011 μM (In each case N=4, i.e. means±SEM from 4 independent series of experiments, which were carried out in triplicate parallel studies).

A detailed description of the method is contained in the publication by Frink, M. Ch., Hennies, H. -H., Englberger, W. et al. (Arzneim.-Forsch./Drug Res. 46 (III), 11, 1029-1036) (the experiment can also be carried out on microtitre places (250 μl/well) at room temperature.

Evaluations:

In addition to % inhibitions at fixed test substance concentrations (e.g. $1 \times 10^{-6}$ M or $1 \times 10^{-5}$ M in the batch), dose dependencies were also tested. $IC_{50}$ values are obtained here and can be converted into inhibitor constants ($K_1$) by the "Cheng-Prusoff equation" (Cheng, Y. C. and Prusoff, W. H., 1973, Biochem. Pharmacol. 22, 3099-3108). The $IC_{50}$ values were obtained with the aid of the "Figure P" computer program (version 6.0, Biosoft, Cambridge, England). Km values were calculated by the method of Lineweaver, H. and Burk, D. (1934, J. Am. Chem. Soc. 56, 658-666). The "Ligand" computer program (version 4, Biosoft, England) was used to obtain $K_D$ values.

A clear inhibition of the re-uptake of serotonin or noradrenaline was measured for the compounds according to the invention. The results of selected investigations of the inhibition of the re-uptake of 5-HT and NA compared with venlafaxine and duloxetine are shown in the following Table 1.

TABLE 1

| Compound according to Example | 5-HT re-uptake inhibition (10 μmol/l) | NA re-uptake inhibition (10 μmol/l) |
|---|---|---|
| 1 | 83% | 35% |
| 2 | 69% | 15% |
| 6 | 94% | 25% |

TABLE 1-continued

| Compound according to Example | 5-HT re-uptake inhibition (10 μmol/l) | NA re-uptake inhibition (10 μmol/l) |
|---|---|---|
| 7 | 95% | 22% |
| 13 | 38% | 75% |
| 14 | 73% | 27% |
| 15 | 51% | 53% |
| 20 | 82% | 74% |
| 23 | 86% | 50% |
| 24 | 67% | 19% |
| 25 | 47% | 71% |
| 26 | 82% | 28% |
| 27 | 88% | 54% |
| 28 | 83% | 29% |
| 29 | 69% | 64% |
| 31 | 70% | 8% |
| 32 | 78% | 55% |
| 33 | 74% | 50% |
| 38 | 76% | 73% |
| 40 | 79% | 42% |
| 48 | 81% | 82% |
| 49 | 55% | 67% |
| 50 | 54% | 29% |
| 54 | 85% | 17% |
| 55 | 67% | 34% |
| 58 | 84% | 47% |
| 59 | 53% | 48% |
| 60 | 75% | 30% |
| 62 | 77% | 13% |
| 63 | 78% | 18% |
| 64 | 68% | 6% |
| 65 | 54% | −8% |
| 67 | 78% | 59% |
| 68 | 67% | 62% |
| 70 | 89% | 52% |
| 71 | 74% | 77% |
| 72 | 60% | 53% |
| 73 | 89% | 55% |
| 74 | 72% | 56% |
| venlafaxine | 82% | 92% |
| duloxetine | 88% | 87% | b) Investigations of the Analgesic Actions in the Formalin Test in Mice

The formalin test (Dubuisson, D. and Dennis, S. G., 1977, Pain, 4, 161-174) represents a model of acute and chronic pain. The chronic pain component was evaluated in the investigations described here.

A biphase nociceptive reaction which is recorded by observing three behaviour patterns which can be clearly differentiated from one another is induced in freely mobile test animals by a single formalin injection into the dorsal side of a hind paw.

Formalin is administered subcutaneously into the dorsal side of the right hind paw of each animal in a volume of 20 μl and a concentration of 1%.

The specific changes in behaviour which differ from the normal behaviour (score 0), such as raising (score 1) and shaking the paw (score 2) and biting and licking reactions (score 3), are observed and recorded continuously at component intervals of 3 min for up to 60 min after the administration of formalin. The changes in behaviour are weighted in different ways (score 0-3) and a pain rate (PR) is calculated using the following formula:

$$PR = [(T_0 \times 0) + (T_1 \times 1) + (T_2 \times 2) + (T_3 \times 3)]/180.$$

In this formula, $T_0$, $T_1$, $T_2$, $T_3$ each correspond to the time in seconds in which the animal showed the modes of behaviour 0, 1, 2 or 3. The group size is 10 animals (n=10).

On the basis of the PR calculations, the action of the substance was determined as the change from a control in percent. The $ED_{50}$ was determined by means of regression analysis.

A dose-dependent inhibition of the nociceptive behaviour was found for the compound according to Example 1. The results are shown in Table 2.

TABLE 2

Formalin test in mice

| Compound according to Example | Inhibition of the nociceptive behaviour versus control; $ED_{50}$ value or % inhibition |
|---|---|
| 1 | 1.66 mg/kg i.v. |
| 2 | 88% (21.5 mg/kg i.v.) |
| 7 | 2.55 mg/kg i.v. |
| 10 | 66.3% (10 mg/kg i.v.) |
| 20 | 66.5% (10 mg/kg i.v.) |
| 23 | 2.44 mg/kg i.v. |
| 24 | 5.4 mg/kg i.v. |
| 28 | 92.6% (10 mg/kg i.v.) |
| 31 | 89.7% (10 mg/kg i.v.) |
| 32 | 2.77 mg/kg i.v. |
| 50 | 37.0% (21.5 mg/kg i.v.) |
| 65 | −39.4% (4.64 mg/kg i.v.) |
| venlafaxine | 2.60 mg/kg i.v. |
| duloxetine | 6.69 mg/kg i.p. | c) Investigation of the Antidepressant Action in the Forced Swimming Test (Porsolt Test) in Mice The investigations to determine the antidepressant action of the compounds of the formula I according to the invention were carried out in the forced swimming test (Porsolt test) in mice (Porsolt, R. et al., Arch. Int. Pharmacodyn. vol. 229, p. 327-336, (1977)). Male mice (20-25 g body weight) were placed individually for a period of 6 minutes in a shallow bowl of water from which they were unable to escape and were therefore forced to swim. After some time the animals gave up their swimming attempts and passed into an immobility phase. The duration of the immobility phase in the interval of 2-6 minutes after introduction of the animals was determined. The substance and vehicle groups each comprise 10 animals. Changes in the duration of the immobility phase are stated relative to the vehicle control. Differences versus the vehicle control are tested for significance with the aid of the Student's T test. Antidepressants induce a shortening of the immobility phase.

For the compound according to Example 1, a significant shortening of the immobility phase and therefore an antidepressant action was found in the forced swimming test. The results are shown in Table 3.

TABLE 3

Forced swimming test in mice
Change in immobility phase versus control

| Dose | Compound according to Example 1 | Venlafaxine | Duloxetine |
|---|---|---|---|
| 2.15 mg/kg i.p. | −54%*** | −66%*** | −41%** |

Student's T test;
***: p < 0.001 d) Investigation of the Anxiolytic Action in the Isolation-Induced Pup Vocalization Test in Mice The isolation-induced pup vocalization test in mice was used to investigate anxiolytic actions (Fish, E. W., Sekinda, M., Ferrari, P. F., Dirks, A., Miczek, K. A., Psychopharmacology, vol. 149, p. 277-285, (2000)). Litters of 7 to 13 mice were used for the testing. At the age of 7 days the animals were separated from the mother and placed in an incubation cage with an internal temperature of approx. 34° C. For determination of the vocalizations in the ultrasonic range, the animals were placed individually on a temperature-controlled platform (23 cm×23 cm, divided by a grid into fields of 2 cm×2 cm, 19±1° C.) of a soundproofed test chamber for a duration of 30 sec. The ultrasonic vocalizations were recorded with a high-frequency capacitor microphone, filtered, amplified, digitalized and plotted and analysed using commercial software. Only animals with pre-values of at least 6 vocalizations within 30 sec and a body weight of 3.5 to 5.5 g were employed for the testing. After subcutaneous (s.c.) injection of substance or vehicle, the animals were returned to the incubation cage for a duration of 10 min and then placed individually again on the temperature-controlled plate of the test chamber for a duration of 4 min. In addition to the number of vocalizations, crossings of the grid of the plate and body turns of the mice were determined to investigate influences of the substance on locomotor activity and coordination. Changes in the vocalization frequencies, crossings of the grid and body turns were stated relative to the vehicle control. A reduction in the vocalization frequency is described for anxiolytics.

A significant reduction in the vocalization frequency was measured for the compound according to Example 1. After administration of this compound, no significant changes in the crossings of the grid and body turns were observed. A selective anxiolytic action without influencing of locomotion and coordination was thus determined in the isolation-induced pup vocalization test. The results for the compound according to Example 1 and for venlafaxine and citalopram are shown in the following three tables.

TABLE 4

Change in vocalization frequency versus control

|  | Compound according to Example 1 | Venlafaxine | Citalopram |
|---|---|---|---|
| $ED_{50}$ value | 1.7 mg/kg s.c. | 8.1 mg/kg s.c. | 1.2 mg/kg s.c. |

TABLE 5

Change in grid crossings

|  | Compound according to Example 1 | Venlafaxine | Citalopram |
|---|---|---|---|
| Dose range | 1.0-17 mg/kg s.c. | 0.3-56 mg/kg s.c. | 0.56-10 mg/kg s.c. |
| Maximum change | +32% (n.s.) | +92% (n.s.) | +66% (n.s.) |

ANOVA, post-hoc Dunnett's test ($\alpha = 0.05$);
n.s.: not significant;
s.: significant ($p < 0.05$)

TABLE 6

Change in body turns

|  | Compound according to Example 1 | Venlafaxine | Citalopram |
|---|---|---|---|
| Dose range | 1.0-17 mg/kg s.c. | 0.3-56 mg/kg s.c. | 0.56-10 mg/kg s.c. |
| Maximum change | +233% (n.s.) | +141% (n.s.) | +397% (s.) |

ANOVA, post-hoc Dunnett's test ($\alpha = 0.05$);
n.s.: not significant;
s.: significant ($p < 0.05$)

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereto.

What is claimed is:

1. A heteroarylcycloalkylmethyl-amine compound corresponding to formula I

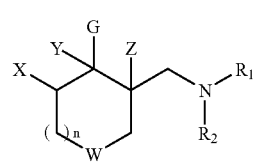

wherein

W is $CH_2$, and Y is chosen from H or Cl and X and Z are H or

X and Y together form a bond and Z is H or

Y and Z together form a bond and X is H, or

W is O, S, SO or $SO_2$, and Y is chosen from H, OH or Cl and X and Z are H or

X and Y together form a bond and Z is H or

Y and Z together form a bond and X is H, and n=0-3, $R^1$ and $R^2$ independently of one another are chosen from H, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, $NH_2$, SH or OH, $OCH_3$ or unsubstituted; $C_3$-$C_7$-cycloalkyl, saturated or unsaturated, mono- or polysubstituted by F, Cl, Br, I, $NH_2$, SH or OH, $OCH_3$ or unsubstituted, or a corresponding heterocyclic radical in which a C atom in the ring is replaced by S, O or $NR^3$, where $R^3$ is chosen from H, $C_1$-$C_{10}$-alkyl, $C_2$-$C_{10}$-alkenyl or $C_2$-$C_{10}$-alkynyl, in each case branched or unbranched, mono- or polysubstituted by F, Cl, Br, I, $NH_2$, SH or OH, $OCH_3$ or unsubstituted;

alkylaryl, saturated or unsaturated, mono- or polysubstituted by F, Cl, Br, I, $NH_2$, SH or OH, $OCH_3$ or unsubstituted; alkylheteroaryl, saturated or unsaturated, mono- or polysubstituted by F, Cl, Br, I, $NH_2$, SH or OH, OCH₃ or unsubstituted, aryl, mono- or polysubstituted by F, Cl, Br, I, NH₂, SH or OH, OCH₃ or unsubstituted;

or $R^1$ and $R^2$ together form a $C_3$-$C_7$-cycloalkyl, saturated or unsaturated, mono- or polysubstituted by F, Cl, Br, I, NH₂, SH or OH, OCH₃ or unsubstituted, or a corresponding heterocyclic radical in which a C atom in the ring is replaced by S, O or $NR^4$, where $R^4$ is chosen from H, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, NH₂, SH or OH, OCH₃ or unsubstituted, and G is chosen from pyridin-3-yl or pyridin-4-yl and is unsubstituted or mono- or polysubstituted, wherein at least one hydrogen radical is replaced by F, Cl, Br, I, CN, CF₃, NO₂, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, NH₂, SH or OH, OCH₃ or unsubstituted; $C_3$-$C_7$-cycloalkyl, saturated or unsaturated, mono- or polysubstituted by F, Cl, Br, I, NH₂, SH or OH, OCH₃ or unsubstituted, or a corresponding heterocyclic radical in which a C atom in the ring is replaced by S, O or $NR^5$, where $R^5$ is chosen from H, $C_1$-$C_{10}$-alkyl, $C_2$-$C_{10}$-alkenyl or $C_2$-$C_{10}$-alkynyl, in each case branched or unbranched, mono- or polysubstituted by F, Cl, Br, I, NH₂, SH or OH, OCH₃ or unsubstituted;

$OR^6$, $OC(O)R^6$, $OC(S)R^6$, $C(O)R^6$, $C(O)OR^6$, $C(S)R^6$, $C(S)OR^6$, $SR^6$, $S(O)R^6$ or $S(O_2)R^6$, wherein $R^6$ is chosen from H, $C_1$-$C_{10}$-alkyl, $C_2$-$C_{10}$-alkenyl or $C_2$-$C_{10}$-alkynyl, in each case branched or unbranched, mono- or polysubstituted by F, Cl, Br, I, NH₂, SH or OH, $OCH^3$ or unsubstituted; $C_3$-$C_7$-cycloalkyl, saturated or unsaturated, mono- or polysubstituted by F, Cl, Br, I, NH₂, SH or OH, OCH₃ or unsubstituted, or a corresponding heterocyclic radical in which a C atom in the ring is replaced by S, O or $NR^7$, where $R^7$ is chosen from H, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, NH₂, SH or OH, OCH₃ or unsubstituted;

alkylaryl, saturated or unsaturated, mono- or polysubstituted by F, Cl, Br, I, NH₂, SH or OH, OCH₃ or unsubstituted; aryl or heteroaryl, in each case mono- or polysubstituted by F, Cl, Br, I, NH₂, SH or OH, OCH₃ or unsubstituted;

$NR^8R^9C(O)NR^8R^9$ or $S(O_2)NR^8R^9$, wherein $R^8$ and $R^9$ independently of one another are chosen from H, $C_1$-$C_{18}$-alkyl, $C_2$-$C_{18}$-alkenyl or $C_3$-$C_{18}$-alkynyl, in each case branched or unbranched, mono- or polysubstituted by F, Cl, Br, I, NH₂, SH or OH, OCH₃ or unsubstituted; $C_3$-$C_7$-cycloalkyl, saturated or unsaturated, mono- or polysubstituted by F, Cl, Br, I, NH₂, SH or OH, OCH₃ or unsubstituted, or a corresponding heterocyclic radical in which a C atom in the ring is replaced by S, O or $NR^{10}$, where $R^{10}$ is chosen from H, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, NH₂, SH or OH, OCH₃ or unsubstituted;

alkylaryl, saturated or unsaturated, mono- or polysubstituted by F, Cl, Br, I, NH₂, SH or OH, OCH₃ or unsubstituted; aryl or heteroaryl, in each case mono- or polysubstituted by F, Cl, Br, I, NH₂, SH or OH, OCH₃ or unsubstituted;

or $R^8$ and $R^9$ together form a $C_3$-$C_7$-cycloalkyl, saturated or unsaturated, mono- or polysubstituted by F, Cl, Br, I, NH₂, SH or OH, OCH₃ or unsubstituted, or a corresponding heterocyclic radical in which a C atom in the ring is replaced by S, O or $NR^{10}$, where $R^{10}$ is chosen from H, $C_1$-$C_{10}$-alkyl, $C_2$-$C_{10}$-alkenyl or $C_3$-$C_{10}$-alkynyl, in each case branched or unbranched, mono- or polysubstituted by F, Cl, Br, I, NH₂, SH or OH, OCH₃ or unsubstituted;

alkylaryl, aryl or heteroaryl, in each case mono- or polysubstituted by F, Cl, Br, I, NH₂, SH or OH, OCH₃ or unsubstituted, or a physiologically tolerated acid salt thereof.

2. The compound of claim 1, wherein said compound is present in the form of a free base.

3. The compound of claim 1, wherein said compound is present in the form of a pure enantiomer or pure diastereoisomer.

4. The compound of claim 1, wherein said compound is present in the form of a mixture of stereoisomers.

5. The compound of claim 1, wherein said compound is present in the form of a racemic mixture.

6. The compound of claim 1, wherein said compound is present in the form of a hydrochloride salt.

7. The compound of claim 1, wherein W is CH₂ and n=0-3.

8. The compound of claim 1, wherein W is O, S, SO or SO₂ and n=0-3.

9. The compound of claim 1, wherein W is O or S and n=0-3.

10. The compound of claim 1, wherein $R_1$ and $R_2$ independently of one another are chosen from H, $C_1$-$C_{10}$-alkyl, alkylaryl, saturated or unsaturated, mono- or polysubstituted by F, Cl, Br, I, NH₂, SH or OH, OCH₃ or unsubstituted; alkylheteroaryl, saturated or unsaturated, mono- or polysubstituted by F, Cl, Br, I, NH₂, SH or OH, OCH₃ or unsubstituted, or $R_1$ and $R_2$ together form a $C_3$-$C_7$-cycloalkyl, saturated or unsaturated, mono- or polysubstituted by F, Cl, Br, I, NH₂, SH or OH, OCH₃ or unsubstituted, and the radical G is unsubstituted or substituted by Cl, Br or $OR_6$, wherein $R_6$ is H or $C_1$-$C_{10}$-alkyl.

11. The compound of claim 1, wherein said compound is selected from the group consisting of:

dimethyl-(2-pyridin-3-yl-cyclohex-1-enylmethyl)-amine and the corresponding dihydrochloride (1)

methyl-(2-pyridin-3-yl-cyclohex-1-enylmethyl)-amine and the corresponding hydrochloride (2)

dimethyl-(2-pyridin-3-yl-cyclohex-2-enylmethyl)amine and the corresponding hydrochloride (4)

dimethyl-(2-pyridin-3-yl-cyclohexylmethyl)-amine and the corresponding hydrochloride; diastereoisomer 1 (6)

dimethyl-(2-pyridin-3-yl-cyclohexylmethyl)-amine and the corresponding hydrochloride; diastereoisomer 2 (7)

benzyl-methyl-(2-pyridin-3-yl-cyclohex-1-enylmethyl)-amine and the corresponding hydrochloride (10)

benzyl-methyl-(2-pyridin-3-yl-cyclohex-2-enylmethyl)-amine and the corresponding hydrochloride (11)

[2-chloro-2-(6-chloro-pyridin-3-yl)-cycloheptylmethyl]-dimethyl-amine and the corresponding hydrochloride (13)

(2-chloro-2-pyridin-3-yl-cyclohexylmethyl)-dimethyl-amine and the corresponding hydrochloride (14)

[2-chloro-2-(6-chloro-pyridin-3-yl)-cyclohexylmethyl]-dimethylamine and the corresponding hydrochloride (15)

mixture of [2-(4-bromo-6-chloro-pyridin-3-yl)-cyclohex-1-enylmethyl]-methyl-amine and [2-(4-bromo-6-chloro-pyridin-3-yl)-cyclohex-2-enylmethyl]-methyl-amine and the corresponding hydrochlorides (20)

dimethyl-(2-pyridin-3-yl-cyclohept-1-enylmethyl)-amine and the corresponding hydrochloride (23)

dimethyl-(2-pyridin-3-yl-cyclohept-2-enylmethyl)-amine and the corresponding hydrochloride (24)

mixture of [2-(6-chloro-pyridin-3-yl)-cyclooct-1-enylmethyl]-dimethyl-amine hydrochloride and [2-(6-chloro-pyridin-3-yl)-cyclooct-2-enylmethyl]-dimethyl-amine hydrochloride (25)

dimethyl-(2-pyridin-3-yl-cycloheptylmethyl)-amine and the corresponding hydrochloride; diastereoisomer 1 (26)

dimethyl-(2-pyridin-3-yl-cycloheptylmethyl)-amine and the corresponding hydrochloride; diastereoisomer 2 (27)

dimethyl-(2-pyridin-3-yl-cyclopent-1-enylmethyl)-amine and the corresponding hydrochloride (28)

dimethyl-(2-pyridin-3-yl-cyclopent-2-enylmethyl)-amine and the corresponding hydrochloride (29)

dimethyl-(2-pyridin-3-yl-cyclopentylmethyl)-amine and the corresponding hydrochloride (31)

dimethyl-(2-pyridin-3-yl-cyclooct-1-enylmethyl)-amine and the corresponding hydrochloride (32)

dimethyl-(2-pyridin-3-yl-cyclooct-2-enylmethyl)-amine and the corresponding hydrochloride (33)

dimethyl-(2-pyridin-3-yl-cyclooctylmethyl)-amine and the corresponding hydrochloride (35)

(2-chloro-2-pyridin-4-yl-cycloheptylmethyl)-dimethyl-amine and the corresponding hydrochloride (36)

dimethyl-(2-pyridin-4-yl-cyclohept-2-enylmethyl)-amine and the corresponding hydrochloride (37)

dimethyl-(2-pyridin-4-yl-cyclohept-1-enylmethyl)-amine and the corresponding hydrochloride (38)

dimethyl-(2-pyridin-4-yl-cyclohex-1-enylmethyl)-amine and the corresponding hydrochloride (39)

mixture of dimethyl-(2-pyridin-4-yl-cyclohex-1-enylmethyl)-amine hydrochloride and dimethyl-(2-pyridin-4-yl-cyclohex-2-enylmethyl)-amine hydrochloride (40)

dimethyl-(2-pyridin-4-yl-cyclooct-1-enylmethyl)-amine and the corresponding hydrochloride (42)

dimethyl-(2-pyridin-4-yl-cyclopent-2-enylmethyl)-amine and the corresponding hydrochloride (43)

dimethyl-(2-pyridin-4-yl-cyclopent-1-enylmethyl)-amine and the corresponding hydrochloride (47)

[2-(6-chloro-pyridin-3-yl)-cyclohept-2-enylmethyl]-dimethyl-amine and the corresponding hydrochloride (48)

[2-(6-chloro-pyridin-3-yl)-cyclohex-1-enylmethyl]-dimethyl-amine and the corresponding hydrochloride (49)

[2-(5-methoxy-pyridin-3-yl)-cyclohex-1-enylmethyl]-dimethyl-amine and the corresponding hydrochloride (54)

[2-(5-methoxy-pyridin-3-yl)-cyclohex-2-enylmethyl]-dimethyl-amine and the corresponding hydrochloride (55)

mixture of [2-(5-methoxy-pyridin-3-yl)-cyclohept-1-enylmethyl]-dimethyl-amine hydrochloride and [2-(5-methoxy-pyridin-3-yl)-cyclohept-2-enylmethyl]-dimethyl-amine hydrochloride (58)

mixture of 5-(2-dimethylaminomethyl-cyclohept-1-enyl)-pyridin-3-ol; hydrochloride and 5-(7-dimethylaminomethyl-cyclohept-1-enyl)-pyridin-3-ol; hydrochloride (59)

[2-(5-methoxy-pyridin-3-yl)-cycloheptylmethyl]-dimethyl-amine and the corresponding hydrochloride (60)

[2-(5-methoxy-pyridin-3-yl)-cyclohexylmethyl]-dimethyl-amine and the corresponding hydrochloride (62)

mixture of [2-(5-methoxy-pyridin-3-yl)-cyclohexylmethyl]-dimethyl-amine(diastereoisomer 1) and [2-(5-methoxy-pyridin-3-yl)-cyclohexylmethyl]-dimethyl-amine(diastereoisomer 2) and the corresponding hydrochlorides (63)

5-(2-dimethylaminomethyl-cyclohex-1-enyl)-pyridin-3-ol and the corresponding hydrochloride (64)

dipropyl-(2-pyridin-3-yl-cyclohex-1-enylmethyl)-amine and the corresponding hydrochloride (65)

dipropyl-(2-pyridin-3-yl-cyclohex-2-enylmethyl)-amine and the corresponding hydrochloride (66)

[2-(5-methoxy-pyridin-3-yl)-cyclooct-1-enylmethyl]-dimethyl-amine hydrochloride and [2-(5-methoxy-pyridin-3-yl)-cyclooct-2-enylmethyl]-dimethyl-amine and the corresponding hydrochlorides (67)

[2-(6-chloro-pyridin-3-yl)-cyclohex-1-enylmethyl]-dimethyl-amine and the corresponding hydrochloride (68)

[2-(6-chloro-pyridin-3-yl)-cyclohex-2-enylmethyl]-dimethyl-amine and the corresponding hydrochloride (69)

[2-(5-methoxy-pyridin-3-yl)-cyclooctylmethyl]-dimethyl-amine and the corresponding hydrochloride; diastereoisomer 1 (70)

[2-(6-chloro-pyridin-3-yl)-cyclooct-2-enylmethyl]-dimethyl-amine and the corresponding hydrochloride (71)

[2-(5-methoxy-pyridin-3-yl)-cyclooctylmethyl]-dimethyl-amine and the corresponding hydrochloride; diastereoisomer 2 (72)

[2-(5-methoxy-pyridin-3-yl)-cyclooct-2-enylmethyl]-dimethyl-amine and the corresponding hydrochloride (73)

[2-(5-methoxy-pyridin-3-yl)-cyclooct-1-enylmethyl]-dimethyl-amine and the corresponding hydrochloride (74)

5-(7-dimethylaminomethyl-cyclohept-1-enyl)-pyridin-3-ol and the corresponding hydrochloride (75)

5-(2-dimethylaminomethyl-cyclohept-1-enyl)-pyridin-3-ol and the corresponding hydrochloride (76)

5-(2-dimethylaminomethyl-cycloheptyl)-pyridin-3-ol and the corresponding hydrochloride (77) and methyl-(2-pyridin-3-yl-cyclohex-2-enylmethyl)-amine and the corresponding hydrochloride (79).

12. The compound of claim 1, wherein said compound is selected from the group consisting of:

3-dimethylaminomethyl-4-pyridin-3-yl-tetrahydro-thiopyran-4-ol and the corresponding hydrochloride; (50)

3-dimethylaminomethyl-4-pyridin-3-yl-tetrahydro-thiopyran-4-ol and the corresponding hydrochloride; (51)

3-dimethylaminomethyl-4-pyridin-3-yl-tetrahydro-pyran-4-ol and the corresponding hydrochloride (52) and dimethyl-(4-pyridin-3-yl-5,6-dihydro-2H-pyran-3-yl-methyl)-amine and the corresponding hydrochloride (53).

13. A process for preparing a compound according to claim 1 comprising the steps of:

reacting a cycloalkanone of formula II

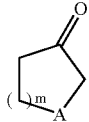

II m = 1-4 wherein A is $CH_2$, O, S, SO or $SO_2$
with immonium salts of formula III

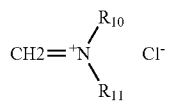

III or with paraformaldehyde and an amine of formula IV,

NHR10R11      IV wherein $R^{10}$ has a meaning the same as $R^1$ and $R^{11}$ has a meaning the same as $R^2$;
reacting the Mannich bases obtained with an organometallic compound of formula V,

V in which Z denotes lithium and V has the meaning of G, in a solvent at between −70° C. and 60° C., wherein the organolithium compound of the formula V, in which Z denotes Li and V has the meaning of G, is prepared by halogen-lithium exchange by reaction of a halogen compound of the formula VI,

VI in which A' denotes Cl, Br or I and V has a meaning the meaning of G, to produce a compound of formula VII,

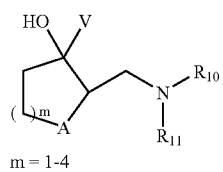

VII m = 1-4 reacting the compound of formula VII with thionyl chloride and
working up the reaction products under basic conditions to produce a mixture of compounds of formulae VIII, IXa and IXb,

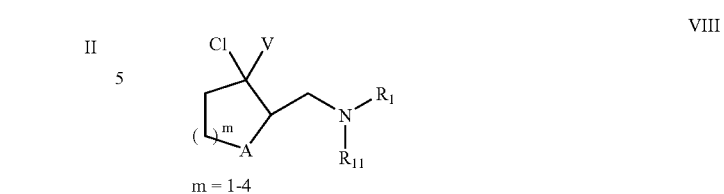

VIII m = 1-4

IXa m = 1-4

IXb m = 1-4 separating the compounds and hydrogenating the compounds corresponding of IXa and IXb with catalytically activated hydrogen, platinum or palladium absorbed on a support material serving as the catalyst, in a solvent under pressures of 0.1 to 10 bar and at temperatures of 20° C. to 80° C. to give a compound of formula X

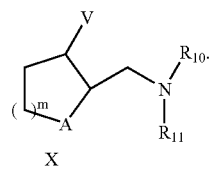

X m = 1-4

14. The process of claim 13, wherein said halogen-lithium exchange involves reacting a halogen compound according to formula VI with n-butyllithium solution.

15. A process according to claim 13, wherein at least one OH group contained in formula I is replaced by an $OSi(Ph)_2$tert-but group, at least one SH group is replaced by an S-p-methoxybenzyl group or at least one $NH_2$ group is replaced by an $NO_2$ group and, after the entire reaction sequence, an $OSi(Ph)_2$tert-but group is split off with tetrabutylammonium fluoride in tetrahydrofuran or at least one p-methoxybenzyl group is split off with a metal amine, or at least one $NO_2$ group is reduced to $NH_2$.

16. A process according to claim 13, wherein after the halogen exchange reaction, a process product having at least one $C(O)OCH_3$ or $C(S)OCH_3$ group is hydrolysed with KOH solution or NaOH solution in methanol at from 40° C.-60° C.

17. A pharmaceutical formulation comprising at least one compound corresponding to claim 1 and a pharmaceutical excipient.

18. The pharmaceutical formulation of claim 17 said pharmaceutical formulation comprising, as an active ingredient, a pharmaceutically effective amount of a compound corresponding to formula I for the treatment of depression, anxiety disorder or pain.

19. A method of alleviating pain in a mammal, said method comprising administering to said mammal an effective pain alleviating amount of a compound according to claim 1.

20. A method for the treatment of depression or anxiety disorder in a mammal, comprising administering to said mammal an effective amount of a compound according to claim 1.

21. The process of claim 15, wherein the metal amine is sodium amine.

* * * * *